United States Patent
Kobayashi

Patent Number: 5,565,015
Date of Patent: Oct. 15, 1996

[54] DISPOSABLE FERMENTER AND FERMENTATION METHOD

[76] Inventor: Fumiko Kobayashi, 1053-42 Asami Kasagake-cho, Nitta-gun Gunma-ken, Japan

[21] Appl. No.: 264,230

[22] Filed: Jun. 23, 1994

Related U.S. Application Data

[63] Continuation of Ser. No. 15,952, Feb. 10, 1993, abandoned.

[30] Foreign Application Priority Data

Feb. 14, 1992 [JP] Japan .................................. 4-059215

[51] Int. Cl.$^6$ .................................. C05F 9/02; C05F 9/04
[52] U.S. Cl. .......................... 71/9; 435/290.1; 435/304.1
[58] Field of Search ................... 71/5, 9, 10; 435/290.1, 435/304.1

[56] References Cited

U.S. PATENT DOCUMENTS

| | | | |
|---|---|---|---|
| 3,724,461 | 4/1973 | Eisenberg | 128/227 |
| 3,934,999 | 1/1976 | Meier | 71/9 |
| 4,100,023 | 7/1978 | McDonald | 71/9 |
| 4,797,367 | 1/1989 | Pinder | 71/9 |

FOREIGN PATENT DOCUMENTS

| | | | |
|---|---|---|---|
| 3726614 | 12/1987 | Germany | 71/9 |
| 0922104 | 4/1982 | U.S.S.R. | 71/8 |

Primary Examiner—Ferris Lander
Attorney, Agent, or Firm—Jordan and Hamburg

[57] ABSTRACT

A disposable fermenter that may be used in the place of a more expensive jar fermenter giving the same performance in a temperature controlled room in place of a sterilized room, with the advantage of not being made of glass which breaks and which may be transported as is, by just sealing the bag.

A flat tube made of plastic film is inserted into the bottom of the bag with the tube sealed to the bag, leaving an opening through the tube so the opening may not be closed. Once the addition of liquid, semi fluid or solid media is made, the breather is set and the bag opening is sealed, the bag is sterilized before or after the bag opening is sealed and the aeration is done through the flat tube.

17 Claims, 3 Drawing Sheets

DISPOSABLE FERMENTER AND FERMENTATION METHOD

This application is a continuation of application Ser. No. 08/015,952 filed Feb. 10, 1993, now abandonded.

BACKGROUND OF THE INVENTION

In the past, glass and stainless steel have been used as the material for fermenters and required at the minimum, aeration sparger and air outlet as well as mixer and sampling port. These fermenters are available in several sizes such as the mini jar fermenter with volumes of 1 to 5 liters made of glass, the jar fermenters made of stainless steel with volumes of 10 to 200 liters and finally even larger fermenters.

The small scale fermenters have been used to generate laboratory data and for fermentation tests and at times, 10 or more are run simultaneously but in general, they are expensive so only a selected number of researchers can use these fermenters.

Recently, more precise and easy control of the temperature in fermentation rooms have become possible due to the efficiency and increased popularity of air conditioners and the size of the fermentation rooms in general have increased. More efficient use of the fermentation rooms by placing numerous identical size fermenters to make more effective use of the space, and simple fermenters with high fermentation efficiency, transportation of the fermentation product, and finally efficient waste disposal of the fermenter are now in demand.

SUMMARY OF THE INVENTION

The present invention has been developed to solve the problem mentioned above. The invention consists of permanently fixing to the bottom of the bag fermenter, a flat plastic film tube which allows free passage through the tube into the bag. The media placed into the bag can be liquid, semi-liquid or solid media. The bag is sealed leaving only the breather open and the media may be sterilized before or after sealing the bag. The aeration is done through the flat plastic tube at the bottom. These are the characteristics of this invention.

The material used to make the fermentation bag should be strong enough to support the weight of the contents of the bag once filled and should be strong enough to withstand pressure sterilization of 125° C. for over 30 minutes. The material should be transparent plastic film made from either polyproplyene, high density polyethylene or polyolefin. The plastic flat tube should be made from the same material as the bag fermenter.

The present invention does not limit the fermentation bag to any particular shape and can be a gusset type bag where both sides of the tube material are folded inward, vertically sealed cylinder type, or a tube type film which has been folded and sealed along the sides, or a cylinder shaped which has been sealed along the sides, or a tube type film with one end sealed. The gusset bag is particularly good because the bottom of the bag when full becomes triangular and keeps the contents from spilling.

A flat plastic tube is inserted into the bottom of the bag prior to sealing the bottom and both sides of the tube in contact with the site to be sealed at the bottom will be sealed with the exception of the inner portion of the tube allowing free passage through the tube into the bag. The flat tube may already have been inserted with a thin stick coated with a material that can be easily pealed off such as fluorine resin or silicone resin. This flat tube may be inserted near the bottom or at the bottom of the vertically sealed bag and fixed. At the same time, the bag may be sealed at the bottom or vertically sealed and then the thin stick may be removed constructing an opening into the bag.

This invention deals with the insertion of a flat tube into the bottom of the bag which acts as a port for passage of air. In general, the flat tube is made of fine film sealed on both ends but also the fine film may be folded with the free sides heat sealed with the other side folded. Moreover, it may be a cylinder type without any sealed portion and the folded side may be sealed at the same time when the bottom of the bag is sealed. However, ideally the flat tube should be sealed on both ends. The port for air passage should be a minimum of 2 cm or ideally larger than 3 cm.

The air port rather than closed may be open but to obtain the most efficient aeration, very small openings in the film may be made near the end of the closed tube.

Since it is difficult to keep the opening of the air port located on the outside of the bag open, it would be best not to seal the tip of the flat plastic tube outside the bag. It may be helpful to change the length of the front and back portions of the tube or to cut the tip of the tube in a zig zag manner.

The breather may be inserted and fixed to the top of the bag in the same way as the air port by using one or more flat plastic tubes. The position of the breather should be such that it will always be above the maximum level of media in the bag. This breather may be used for sampling or may be used as the site for inoculation of microorganisms.

The breather is not absolutely required. The bag opening may be sealed in such a way that there are partial openings. The unsealed portion of the closed opening may be such that it will not interfere in air removal as well as will prevent the contamination from outside, or an opening near the top of the bag which is then wrapped with a special filter.

The air port or breather or both may be inserted with a continuous porous plastic foamed material such as urethane foam or a textile complex material. This material would act as filters and therefore non-sterile air may be used in a non-sterile room without having to worry about contamination. The filter should be made of a hydrophobic material.

The media used in this invention should be composed of material which will allow for uniform distribution of air from the bottom of the bag. Liquid media, fluid or semifluid media may be used. Solid state fermentation media may also be used, but the material must be such that there is room for air to pass through the individual granules.

To make a fermentation using the present invention, a predetermined quantity of media is added to the bag. If the flat plastic tubes are placed as the breathers at the top of the bag, then the opening at the top of the bag may be sealed and a pipe may be inserted into the flat plastic tube. This pipe will insure an opening and then the whole bag may be heat sterilized. After cooling, the media may be inoculated through the breather or the inoculation may take place via a syringe. The sterilization may be accomplished while the top of the bag is open and after inoculation, the top of the bag may be sealed.

In the case where flat plastic tubes are not used as breathers at the top of the bag, the top of the bag can be partially sealed and the distance of this partial seal should be 2.5 cm from the edge of the bag and ideally more than 3 cm. If there is not enough bag film material before the partial opening this can lead to contamination.

The bag opening can be partially sealed two or more times with the open portion staggered. If this is done, the distance between the two should be at a minimum of 1.5 cm and ideally more than 2 cm. The bag opening may be folded twice and then partially sealed. The bag may be sealed before or after sterilization but if the bag is sealed before sterilization, then the inoculation should be done with a syringe.

This present invention deals with the use of a light plastic bag which is the fermenter having a nozzle made of the same material for aeration which is a flat tube. Placing this bag in a temperature controlled room will give the same performance as a jar fermenter as well as being simple and easy to transport. The flat tube will not open by outside forces and will close from the pressure of the inside media, so none of the contents will spill outside. During the fermentation, proper aeration can be maintained through the pipe inserted in the flat tube.

DETAILED DESCRIPTION OF THE PREFERRED EMBODIMENTS

Figure 1:
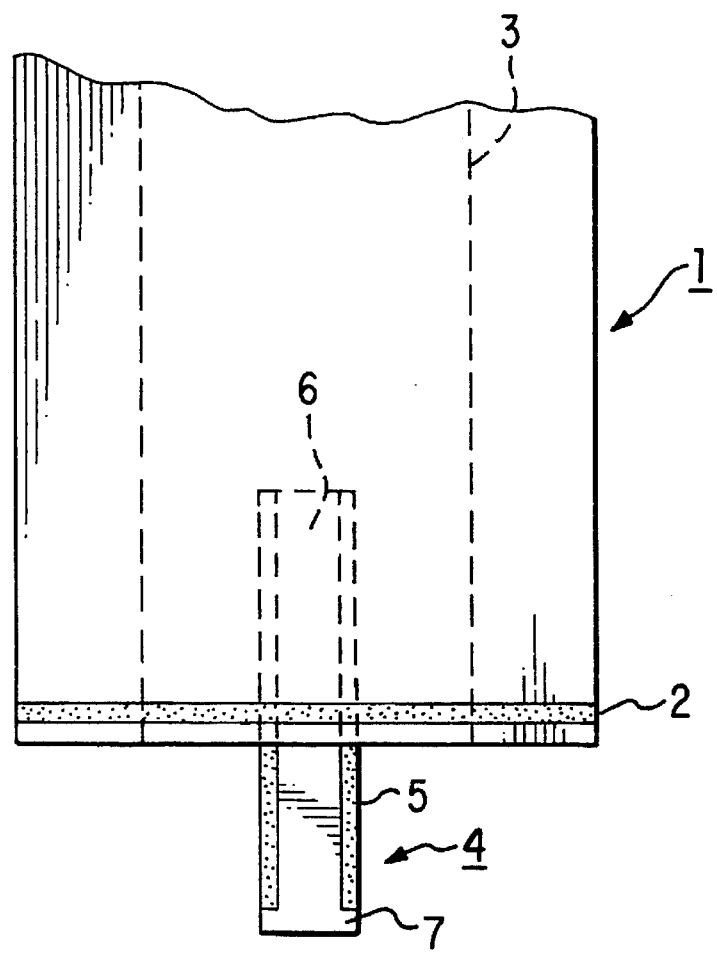
FIG. 1 represents the two dimensional view of the bottom of the bag.

Referring to FIG. 1 fermenter bag, 1 has a sealed portion 2 on the bottom and a folded portion 3 of the gusset. To the sealed site of the bottom of the bag 2, the flat tube 4 is inserted and fixed. Two pieces of film 5 are sealed at both lengths with the opening in the middle 6. The open end of the tube 7 outside the bag is not sealed.

Figure 2:
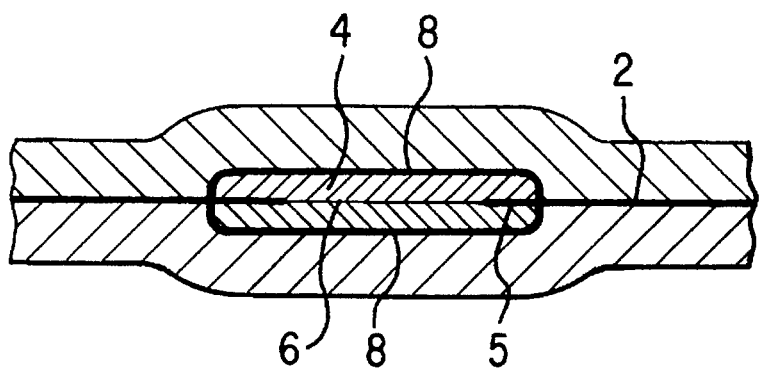
FIG. 2 represents the cross-section 21 view of the method of fixing the flat tube to the bag fermenter.

In FIG. 2, the sealed portion 8 of the flat tube 4 and the film of the bag is illustrated. When the flat tube 4 is inserted and the bottom of the bag is sealed, four pieces of film will be sealed together. To make certain the opening 6 is created, a TEFLON sheet is inserted prior to the sealing process and removed after the sealing process. In FIG. 2, the inner opening is closed, but with internal pressure the opening will open easily.

Figure 3:
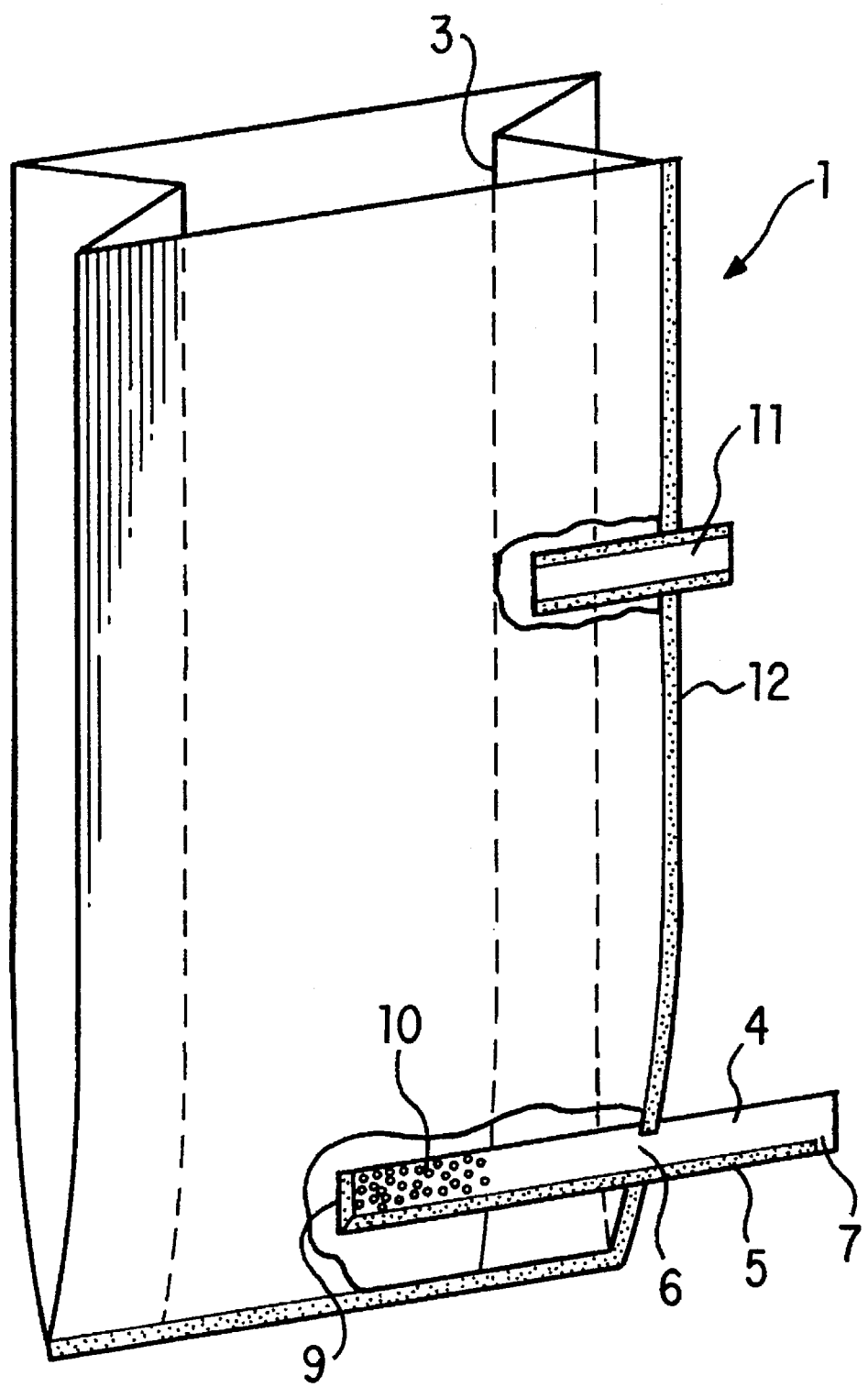
FIG. 3 represents another variation of the invention (shashizu).

In FIG. 3, the flat tube 4 placed at the bottom of the bag 1 is sealed on only one side 5 and the end 9 of the flat tube inside the bag is sealed. Near the end 9 of the flat tube 4 super fine holes 10 are made. From the flat tube 4, air can pass into the bag and the air will enter the bag as small bubbles.

The breather 11 is made of the same material as the flat tube shown in FIG. 1 and is sealed near the top of the vertical sealed side 12. With this bag, fermentation is started by first introducing the media, then the top is sealed, sterilized, and inoculation is made through the breather 11. The air is introduced into the bag through the flat tube 4 and the air is released through the breather 11. Moreover, after fermentation the bag may easily be transported without concern of spillage. For added protection, the outer portion of the flat tube may be sealed after fermentation.

Figure 4:
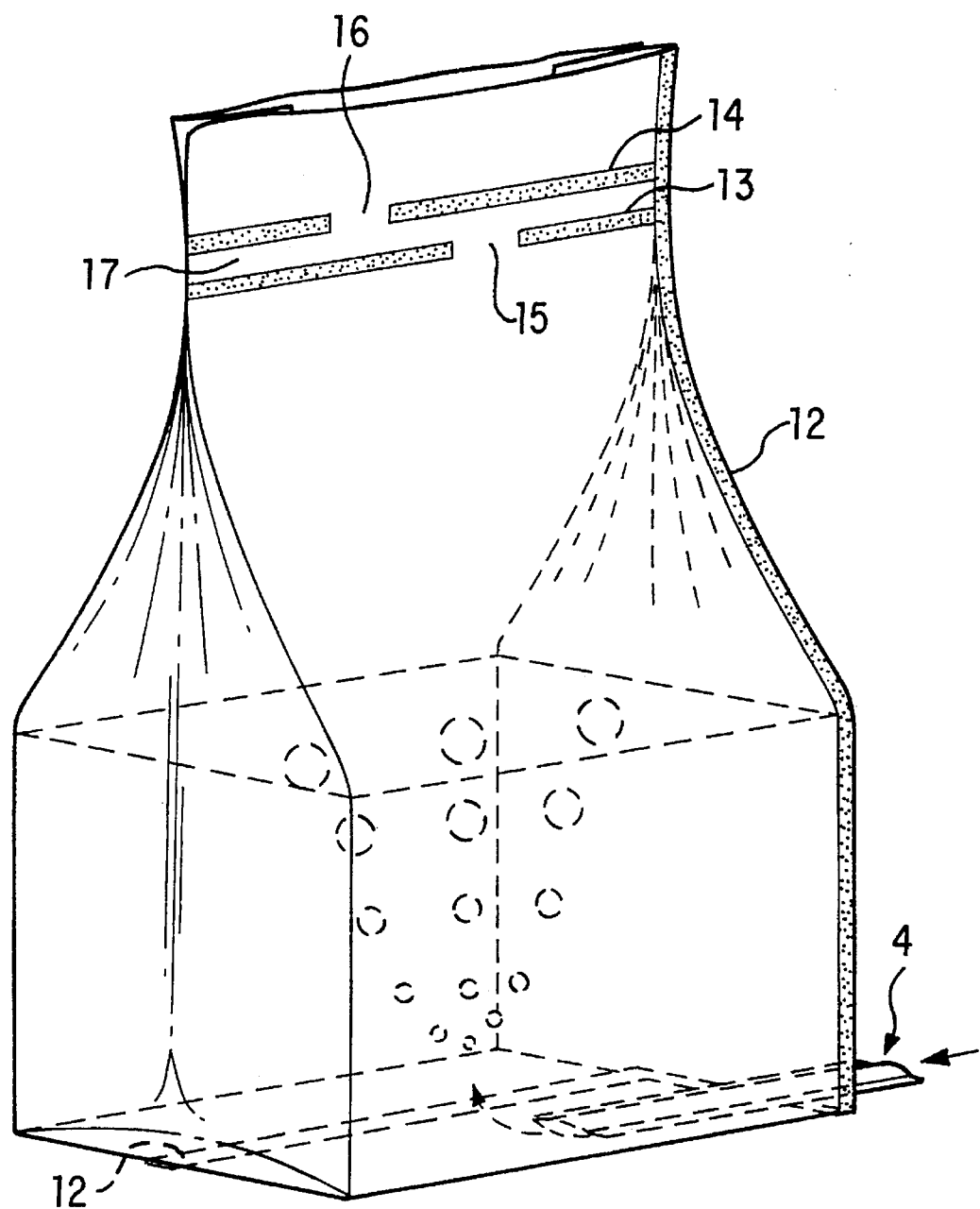
FIG. 4 represents the bag under fermentation conditions.

FIG. 4 is a three dimensional illustration of a bag almost identical to FIG. 3 without the breather 11. There needs to be an opening to release the air coming from the flat tube 4 and to release the steam generated after the bag is filled with media and sterilized. This opening (breather) is constructed by partial sealing of the top of the bag as shown in FIG. 4.

In FIG. 4, the two sealed lines 13, 14 which are about 2 cm apart have the partial openings staggered. The distance from the top of the bag to the sealed line 14 is 5 cm. The air within the bag will first pass through the opening 15, through the space between the two sealed lines 17 and finally to the outside through opening 16. If the pressure inside the bag drops, the two sides of the film opening close and stop the escape of air the outside as well as prevent the outside air to from entering the bag and contaminating it.

EXAMPLE 1

The media composition shown below was placed into a 60 micron thick polyproplyene bag as shown in FIG. 3.

| Potato treated by mixer | 400 g |
|---|---|
| Glucose | 60 g |
| Yeast extract | 6 g |
| Malt extract | 6 g |
| Distilled water | 1,000 ml |
| pH 5.5 | |

The bag was then sealed at the top, glass wool was inserted into the breather 11 and sterilized for 20 minutes at 120° C. The steam generated during the sterilization did not rupture the bag but easily passed through the breather 11. After cooling, 20 g of maitake inoculum prepared beforehand was inoculated through the breather 11. The bag was set in a 24° C. room and sterilized air was supplied through the flat tube 4 at a speed of 2,000 ml/minute.

After 7 to 10 days, uniform mycelia development of the maitake was observed and this was determined to be appropriate for use as the inoculum for inoculating the sawdust. Furthermore, this inoculum may be transported or distributed in the bag and provides the ability to offer liquid inoculum to the mushroom cultivators.

EXAMPLE 2

| Saw dust (broad leaf trees) | 8 liters |
|---|---|
| Wheat bran | 1 liter |
| Moisture adjusted to 65% | |

The above media was placed into the FIG. 4 bag and the top was sealed as shown in the figure. The bag was sterilized for 60 minutes at 120° C., cooled, and 10 g of maitake inoculum was inoculated. The bag was set in a 24° C. room with sterilized air supplied at a rate of 50 ml/minute. After 20 days, the media will be covered with mycelium. The bag is transferred to an 18° C. room and after 30–35 days 400 g–500 g of maitake can be harvested. This production cycle is less than the 45–75 days required by conventional cultivation methods.

The present invention involves the use of an easy to use disposable bag to be incubated in a temperature controlled room without the need for a clean room, giving performance comparable to an expensive jar fermenter. Moreover, the bag may not be easily ruptured and may be transported as is after sealing. Once the bag is finished, it may easily be discarded and will be of benefit in a distribution system.

This invention allows for the fermentation of fungi and bacteria requiring aeration with results comparable to the jar fermenter and it is lightweight, simple, easy to transport, and easy to use disposable fermenter.

What is claimed is:

1. A disposable fermenter comprising a fermenting bag for containing a medium, the fermenting bag having a flat tube affixed at a bottom or lower portion of the bag and at least one means for breathing inserted and fixed to the bag at a position where the means for breathing is always above a maximum level of the medium contained in the bag, the bag being made of a plastic film, the flat tube being made of a plastic film and extending inwardly into the bag and outwardly from the bag, the flat configuration and position of the tube preventing the egress of the medium from the bag and the ingress of contamination into the bag by pressure exerted on the tube by the medium while permitting aeration.

2. A disposable fermenter according to claim 1 wherein an air permeable filter is located inside the flat plastic tube.

3. A disposable fermenter according to claim 1, wherein the plastic film of the bag withstands pressure sterilization at 125° C. for greater than thirty minutes.

4. A disposable fermenter according to claim 1, wherein the plastic film of the bag and of the tube is a transparent plastic film selected from the group consisting of polypropylene, high density polyethylene and polyolefin.

5. A disposable fermenter according to claim 1, wherein a portion of the tube extending inwardly into the bag has a plurality of holes.

6. A process for fermenting using the disposable fermenter of claim 1, comprising sealing the bag, sterilizing a medium contained in the bag, inoculating the medium contained within the bag with microorganisms and continuously supplying air through the flat plastic tube.

7. A disposable fermenter according to claim 1, wherein the bag includes means for independently standing in an upright position.

8. A disposable fermenter according to claim 1, wherein the bag has four side walls and a bottom.

9. A disposable fermenter comprising a fermenting bag for containing a medium, the fermenting bag having a flat tube affixed at a bottom or lower portion of the bag and a staggered seal to an upper portion of the bag resulting in an opening which permits the egress of gas and prevents the ingress of contamination, the bag being made of a plastic film, the flat tube being made of plastic film and extending inwardly into the bag and outwardly from the bag, the flat configuration and position of the tube preventing the egress of the medium from the bag and the ingress of contamination into the bag, by pressure exerted on the tube by the medium, while permitting aeration.

10. A disposable fermenter according to claim 9, wherein the staggered seal comprises two parallel sealed lines horizontally aligned with the upper portion of the bag, the two sealed lines each having a portion thereof which is unsealed, the unsealed portion of one sealed line is not vertically aligned with the unsealed portion of the other sealed line.

11. A disposable fermenter according to claim 9, wherein an air permeable filter is located inside the flat plastic tube.

12. A process for fermenting using the disposable fermenter of claim 9, comprising sealing the bag, sterilizing a medium contained in the bag, inoculating the medium contained within the bag with microorganisms and continuously supplying air through the flat plastic tube.

13. A disposable fermenter according to claim 9, wherein the bag includes means for independently standing in an upright position.

14. A disposable fermenter according to claim 9, wherein the bag has four side walls and a bottom.

15. A disposable fermenter according to claim 9, wherein the plastic film of the bag withstands pressure sterilization at 125° C. for greater than thirty minutes.

16. A disposable fermenter according to claim 9, wherein the plastic film of the bag and of the tube is a transparent plastic film selected from the group consisting of polypropylene, high density polyethylene and polyolefin.

17. A disposable fermenter according to claim 9, wherein a portion of the tube extending inwardly into the bag has a plurality of holes.

* * * * *